United States Patent
Yang et al.

(10) Patent No.: US 10,758,146 B2
(45) Date of Patent: Sep. 1, 2020

(54) SYSTEM AND METHOD FOR FETAL HEARTBEAT SOUND MONITORING AND RECORDING BY PROPAGATION AND SPACIAL LOCATION ANALYSIS BY A SENSOR MATRIX

(71) Applicants: Qinshan Yang, Katy, TX (US); Qingquan Zhang, Katy, TX (US)

(72) Inventors: Qinshan Yang, Katy, TX (US); Qingquan Zhang, Katy, TX (US)

(*) Notice: Subject to any disclaimer, the term of this patent is extended or adjusted under 35 U.S.C. 154(b) by 115 days.

(21) Appl. No.: 15/951,704

(22) Filed: Apr. 12, 2018

(65) Prior Publication Data

US 2018/0296116 A1  Oct. 18, 2018

Related U.S. Application Data

(60) Provisional application No. 62/484,640, filed on Apr. 12, 2017.

(51) Int. Cl.

| | |
|---|---|
| *A61B 5/02* | (2006.01) |
| *A61B 8/02* | (2006.01) |
| *A61B 8/08* | (2006.01) |
| *A61B 8/00* | (2006.01) |
| *A61B 5/0448* | (2006.01) |
| *A61B 5/024* | (2006.01) |
| *A61B 5/00* | (2006.01) |

(52) U.S. Cl.
CPC ........ *A61B 5/0448* (2013.01); *A61B 5/02411* (2013.01); *A61B 5/4356* (2013.01); *A61B 8/0866* (2013.01); *A61B 8/4227* (2013.01); *A61B 8/4494* (2013.01); *A61B 5/4362* (2013.01); *A61B 8/488* (2013.01); *A61B 2503/02* (2013.01)

(58) Field of Classification Search
CPC .. A61B 5/024; A61B 5/03; A61B 5/11; A61B 5/02411; A61B 5/113; A61B 5/4356; A61B 5/4362; A61B 5/6831
USPC ................................ 600/588, 528, 500, 595
See application file for complete search history.

(56) References Cited

U.S. PATENT DOCUMENTS

| | | | |
|---|---|---|---|
| 4,086,917 A | 5/1978 | Burks et al. | |
| 4,890,624 A | 1/1990 | Ganguly et al. | |
| 5,170,791 A | 12/1992 | Boos et al. | |
| 5,365,937 A | * 11/1994 | Reeves | A61B 7/003 600/528 |
| 5,524,631 A | 6/1996 | Zahorian et al. | |
| 5,817,035 A | * 10/1998 | Sullivan | A61B 5/02411 600/588 |
| 6,245,025 B1 | 6/2001 | Torok et al. | |
| 2010/0016744 A1 | 2/2010 | Brost et al. | |

(Continued)

*Primary Examiner* — Jon Eric C Morales
(74) *Attorney, Agent, or Firm* — Egbert, McDaniel & Swartz, PLLC

(57) ABSTRACT

A system for monitoring a fetal heartbeat sound has a sensor matrix adapted to be placed adjacent to a fetus, a processor for receiving signals transmitted by the sensor matrix, a processor for receiving signals transmitted by the sensor matrix, and a display connected to the processor so as to provide a humanly perceivable indication of the heartbeat sound. The sensor matrix has a plurality of sensors of which at least one of which is facing the fetus. The processor identifies a fetal heartbeat sound from among other sounds. The sensor array is affixed to a wearable article that is adapted to be worn by mother.

17 Claims, 7 Drawing Sheets

(56) References Cited

U.S. PATENT DOCUMENTS

| | | |
|---|---|---|
| 2010/0168596 A1 | 7/2010 | Jaeschke et al. |
| 2011/0160591 A1 | 6/2011 | Smith et al. |
| 2013/0331704 A1* | 12/2013 | Salzman .............. A61B 8/0866 600/459 |
| 2014/0031707 A1 | 1/2014 | Rao et al. |
| 2014/0276070 A1 | 9/2014 | Kabakov et al. |
| 2016/0213349 A1 | 7/2016 | Groberman et al. |
| 2016/0270685 A1 | 9/2016 | Oz et al. |
| 2018/0368753 A1* | 12/2018 | Yin ......................... A61B 7/00 |

* cited by examiner

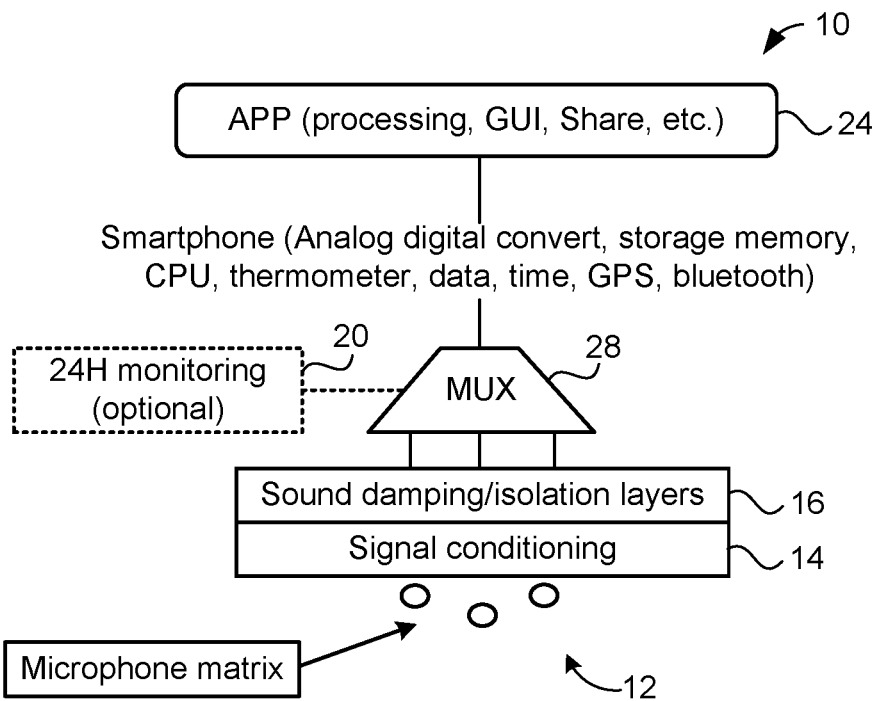
FIG. 1
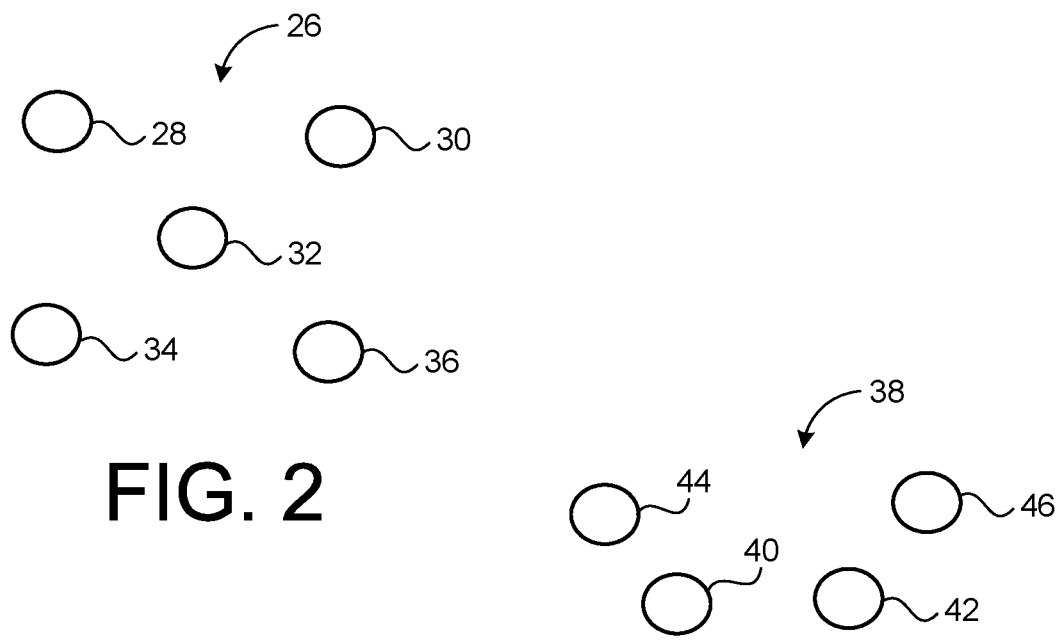
FIG. 2
FIG. 3

SYSTEM AND METHOD FOR FETAL HEARTBEAT SOUND MONITORING AND RECORDING BY PROPAGATION AND SPACIAL LOCATION ANALYSIS BY A SENSOR MATRIX

CROSS-REFERENCE TO RELATED APPLICATIONS

The present application claims priority from U.S. Provisional Patent Application Ser. No. 62/484,640, filed on Apr. 12, 2017, and entitled "Apparatus and Method for Fetal Heartbeat Sound Monitoring and Recording by Propagation and Spatial Location Analysis by a Microphone Matrix".

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the monitoring of fetal heartbeat sounds. More particularly, the present invention relates to the use of a sensor matrix for monitoring fetal heartbeat sounds. More particularly, the present invention relates to a smartphone-based system for monitoring and recording fetal heartbeat sounds, uterine contraction and fetal movement.

2. Description of Related Art Including Information Disclosed Under 37 CFR 1.97 and 37 CFR 1.98

In recent years, medicine has made significant advances in many areas related to the care of mothers and their babies. It has been found that by monitoring the fetus, doctors can be provided with a continuous and highly accurate report on the most widely used indicator of fetal condition, i.e. the fetal heartbeat sound. By monitoring the fetal heartbeat sound, uterine contraction and fetal movement, doctors have been able to decrease the need for emergency Cesarean sections. This decrease has been made possible by conservative measures such as changing the maternal position to relieve pressure on the umbilical cord. Additionally, mothers often desire to monitor the heartbeat sound of the fetus in order to determine the development of the fetus during pregnancy and the condition of the fetus.

Various apparatus have been used for monitoring the fetal heartbeat sound. For example, stethoscopes have been used to listen to the fetal heartbeat. This particular means for monitoring the heartbeat sound has been unsatisfactory during periods of labor contractions due to the high degree of extraneous or artifact noise. Since fetal distress is apt to occur during labor contractions, the stethoscopic means for monitoring the heartbeat sound has not provided a satisfactory indication of fetal condition.

The heartbeat sound of the fetus has also been monitored using various electronic apparatus to determine certain characteristics of the heartbeat. This is usually accomplished using two electrodes one of which is attached to the head of the fetus. Although this technique provides reasonably accurate data, there are obvious disadvantages. For example, the electrode cannot be attached to the head of the fetus until the cervix has opened sufficiently and the amniotic sack has been ruptured. For obvious reasons, this technique has not been used for monitoring the fetus during pregnancy or in the early stages of late labor. In addition, the electrode that has to be applied either blindly or using a special light source that requires special training. Furthermore, the presence of a doctor has been required to supervise the electrode attachment.

Ultrasonic transducers have also been used for monitoring the fetal heartbeat sound. These transducers have transmitted an ultrasonic signal which has been reflected by the motion of tissue, such as the heart, to produce a Doppler effect and a corresponding electrical signal in the transducer. Since any movement of tissue within the path of the transmitted ultrasonic signal produces characteristics and the corresponding electrical signal, the particular characteristics associated with the heartbeat are disguised as a high degree of extraneous or artifact noise.

The resulting electrical signal is of relatively low power and the characteristics of particular interest are of relatively low frequency. As a result, it has been particularly difficult to isolate the signals from the spurious low-frequency signals in the atmosphere, such as those transmitted by frequency modulated radio stations. Monitors of the prior art receiving these crude signals have been unable to satisfactorily separate the characteristics relating to the heartbeat sound from the characteristics relating to the artifact noise and radio interference.

In the past, various patents and patent publications have issued with respect to the monitoring of fetal heartbeat sounds. For example, U.S. Pat. No. 4,086,917, issued on May 2, 1978 to Burks et al., shows a fetal heartbeat sound monitoring system including ultrasonic transducers arranged in an array. Each ultrasonic transducer provides a particular signal having characteristics related to the heartbeat sound of an associated fetus. Each particular signal is processed at an associated labor room monitor and modulated on a different carrier frequency for transmission on power lines in the hospital. At a remote location, the nurse's station power unit is modular with the nurse's station monitors. The line signals are individually demodulated in an associated one of the nurses station monitors to provide an indication of heartbeat sound. The transducer assemblies are shielded to inhibit interference of spurious low-frequency signals.

U.S. Pat. No. 4,890,624, issued on Jan. 2, 1992 to Ganguly et al., describes a fetal heartbeat sound counting system that uses digital signal processing. The fetal heartbeat sound counting system includes a transducer element for transmitting an ultrasound signal into the fetal heart while the fetus is in utero and for receiving and returning a Doppler signal frequency shifted by the action of the fetal heart. The returning Doppler signal is processed produce a forward heart movement Doppler signal, a reverse heart movement Doppler signal, and the complete Doppler signal, from each of which the fetal heartbeat sound data is obtained. A composite fetal heartbeat sound data is then produced from the three processed Doppler signals.

U.S. Pat. No. 5,170,791, issued on Dec. 15, 1992 to Boos et al., teaches a method and apparatus for calculating the fetal heartbeat sound. The moving parts of the fetal heart cause a Doppler shift which is used to determine the fetal heartbeat sound via an autocorrelation function. The moving parts of the fetal heart with different velocities and Doppler shifts originating from other physiological sources generate secondary maximia in the autocorrelation function so that an accurate heartbeat sound determination would become nearly impossible. The method overcomes this by parallel processing of the demodulated ultrasound signal in various pass-bands and the signal is fed to filters of different frequency characteristics. The output of the pass-bands is used for the fetal heartbeat sound calculation.

U.S. Pat. No. 5,524,631, issued on Jun. 11, 1996 to Zohorian et al., provides a passive fetal heartbeat sound monitoring apparatus and method with enhanced fetal heart beat discrimination. Multiple sensor signals are outputted by a passive fetal heartbeat sound monitoring sensor. Multiple parallel nonlinear filters filter these multiple sensor signals to identify fetal heartbeats in the signal data. A processor determines a fetal heartbeat sound based on these identified fetal heartbeats. The processor includes the use of a figure of merit weighting of heartbeat sound estimates based on the identified heartbeats from each filter for each signal. The fetal heartbeat sound that is determined is outputted to a display, a storage, or to a communications channel.

U.S. Pat. No. 6,245,025, issued on Jun. 12, 2001 to Torok et al., describes a method and apparatus for long-term, non-invasive measurement of fetal heartbeat sound. The method utilizes the characteristic curves of first and second heart sounds received by electro-acoustical converters. The identification and distinction of first and second sounds and furthermore their time relation used for heartbeat identification increases the reliability of fetal heartbeat sound determination. The distinction of first and second sounds is based on the differences in the frequency spectrum as measured in a relatively short-time window and by the estimation of the power peaks measured on two test frequencies chosen on the two ends of the frequency range of fetal heart sound. Digital filtering and selective power estimation is applied for continuous computation of power/time function on the two test frequencies.

U.S. Patent Application Publication No. 2010/0016744, published on Jan. 21, 2010 to Brost et al., provides a fetal heartbeat sound monitoring system that includes an ultrasonic transducer for transmitting a signal to a patient and for receiving a reflected heartbeat monitoring signal. A monitoring system is coupled to the ultrasonic transducer so as to process the heartbeat monitoring signal and process heartbeat information representative of the monitored heartbeat sound. A mechanical or electronic steering system is coupled to the ultrasonic transducer so as to control the location of signal transmitted to the patient and/or the location of the received heartbeat monitoring signal.

U.S. Patent Application Publication No. 2010/0168596, published on Jul. 1, 2010 to Jaescke et al., discloses a method of monitoring a fetal heartbeat sound. This method comprises providing a first measurement head and a second measurement head and a sensor. The sensor is adapted to sense the maternal heartbeat sound. The first measurement head is adapted to sense maternal-fetal-related medical data. The second measurement head is adapted to sense the fetal heartbeat sound.

U.S. Patent Application Publication No. 2011/0160591, published on Jun. 30, 2011 to Smith et al., teaches a fetal heartbeat sound monitor with a wide search area. A continuous, non-invasive fetal heartbeat sound measurement is produced using an ultrasound probe positioned on the abdomen of the mother. The ultrasound probe includes a plurality of ultrasound transducers that are positioned within a housing having a transmission surface. The transmission surface is configured to defocus the individual ultrasound beams created by the plurality of ultrasound transducers. The transmission surface defocuses the ultrasound beam and creates a wider area of coverage for the ultrasound probe.

U.S. Patent Application Publication No. 2014/0031707, published on Jan. 30, 2014 to Rao et al., provides an apparatus and method for automatically identifying a fetal heartbeat sound baseline. This apparatus and method includes collecting fetal heartbeat sound data within a preset duration to obtain a fetal heartbeat sound data sequence, preprocessing the collected fetal heartbeat sound data sequence to obtain a corresponding fetal heartbeat sound data sequence during preprocessing, selecting a primary dominant peak value according to the frequency distribution of the corresponding fetal heartbeat sound data sequence during the preprocessing, and identifying a dynamic baseline according to the corresponding fetal heartbeat sound data sequence and the primary dominant peak value during the preprocessing to obtain the dynamic baseline. The dynamic baseline is displayed and printed.

U.S. Patent Application Publication No. 2014/0276070, published on Sep. 18, 2014 to Kabakov et al., discloses a method and device for monitoring a fetal heartbeat sound. This method and device includes a reference fetal heartbeat sound detected across an ultrasound depth zone of sensitivity. The ultrasound depth zone of sensitivity is scanned in overlapping increments of a first depth. An average fetal heartbeat sound detected by each overlapping increment is tested for a coincidence with the referenced fetal heartbeat sound. Overlapping increments with the coincidence and a maximize signal quality rate are identified. An ultrasound depth increment of a second depth is selected representing the selected adjacent increments. Fetal heartbeat sound is determined from the ultrasound signal returned from a scanned depth of the second depth.

U.S. Patent Application Publication No. 2016/0213349, published on Jul. 28, 2016 to Groberman et al., teaches a fetal heartbeat sound monitoring system. This fetal heartbeat sound monitoring system has at least one Doppler transducer, at least one processor, and at least one communication module. The fetal heartbeat sound is obtained by at least one Doppler transducer. The Doppler transducer has a high-frequency mode and a low-frequency mode. The Doppler transducer is placed around the abdomen of an expectant mother. The Doppler transducer is set to the low-frequency mode. The low-frequency mode has a wide beam that facilitates the location of the fetal heartbeat. The Doppler transducer is moved past the abdomen to a location where the fetal heartbeat signal is found. The Doppler transducer is then switched to the high frequency mode while keeping the Doppler transducer in the location for receiving the fetal heartbeat signal.

It is an object of the present invention to provide a method and apparatus for fetal heartbeat sound monitoring which is passive.

It is another object of the present invention to provide an apparatus and method for fetal heartbeat sound monitoring that does not utilize any radiation.

It is another object advantage of the present invention to provide an apparatus and method for fetal heartbeat sound monitoring that is convenient.

It is another object of the present invention to provide an apparatus and method for fetal heartbeat sound monitoring, uterine contraction monitoring and fetal movement that allows for the simple use of a smartphone.

It is another object of the present invention to provide a method and apparatus for fetal heartbeat sound monitoring that is multi-functional.

It is another object of the present invention to provide a method and apparatus for fetal heartbeat sound monitoring that uses a simple sensor matrix to separate heartbeat sounds from other sounds in an area around the fetus.

It is another object of the present invention to provide an apparatus and method for fetal heartbeat sound monitoring that is accurate.

It is another object of the present invention to provide an apparatus and method for fetal heartbeat sound monitoring that is adaptable to various fetal positions.

It is still another object of the present invention to provide an apparatus and method for fetal heartbeat sound monitoring which provides a full waveform.

It is still another object of the present invention to provide a method and apparatus for fetal heartbeat sound monitoring that effectively cancels background noise.

It is another object of the present invention to monitor fetal movement of multiple fetuses.

These and other objects and advantages of the present invention will become apparent from a reading of the attached specification and appended claims.

BRIEF SUMMARY OF THE INVENTION

The present invention is a system for monitoring a fetal heartbeat sound. The system comprises a sensor matrix adapted to be placed adjacent to a fetus, a processor for receiving signals transmitted by the sensor matrix, and a display connected to the processor so as to provide a humanly perceivable indication of the heartbeat sound. The sensor matrix has a plurality of sensors of which at least one sensor is facing the fetus. The processor is adapted to identify a fetal heartbeat sound from among other sounds.

The plurality of sensors have at least one sensor is facing the fetus. The plurality of sensors are arranged in spaced relation to each other.

The system of the present invention can include a wearable article adapted to be worn by mother. The sensor array is affixed to the wearable article. In particular, the wearable article can be a belly band adapted to be wrapped around a stomach of the mother. Another wearable article can be positioned in spaced relation to the belly band. The sensor array can be attached to the pants or bra of the mother, alternatively. At least one of the plurality of sensors is affixed to this another wearable article.

Each of the plurality of sensors includes an metal disk. A distributed square or circular-shaped piezoelectric sensor is on top of the metal disk. Dampening materials positioned between the piezoelectric sensors. A sound dampening layer is interposed between the wearable article and a back surface of the metal disk. The sound dampening material can include a rubber material layer positioned adjacent to the wearable article and a polymeric layer positioned adjacent to the sensor. The rubber material layer is affixed to the polymeric layer.

A signal conditioner is connected to the sensor so as to create a full waveform of sound. Each sensor of the plurality of sensors is a piezoelectric sensor. The sensor array can be in a trapezoidal pattern or a cruciform pattern. The plurality of sensors of the sensor array can have one sensor facing a heart of a mother so as to sense a heartbeat of the mother. Another sensor of the plurality of sensors can face an environment adjacent to the mother so as to sense background noise. A multiplexer or is connected by wires or wirelessly to the sensor array. A smartphone or personal digital assistant (PDA) is connected to the multiplexer so as to process signals from the multiplexer so as to isolate the fetal heartbeat sound from the heartbeat of the mother and from background noise.

The present invention is also a method of monitoring a fetal heartbeat. This method includes the steps of: (1) positioning a sensor array onto a body of a mother in proximity to a fetus; (2) detecting the fetal heartbeat sound and a heartbeat sound of the mother and environmental sound by the sensor array; (3) transmitting a plurality of signals from the sensor array to a processor; (4) processing the plurality of signals so as to isolate the fetal heartbeat sound from the heartbeat sound of the mother and the environmental sound; and (5) displaying an indication of the fetal heartbeat sound from the processed plurality of signals.

In this method, another sensor can be positioned in proximity to a heart of the mother. The sensor array can be affixed to a wearable article such that the sensor array is interposed between the wearable article and the body of the mother.

This foregoing Section is intended to describe, with particularity, the preferred embodiments of the present invention. It is understood that modifications to these preferred embodiments can be made within the scope of the present claims. As such, this Section should not to be construed, in any way, as limiting of the broad scope of the present invention. The present invention should only be limited by the following claims and their legal equivalents.

BRIEF DESCRIPTION OF THE SEVERAL VIEWS OF THE DRAWINGS

FIG. 1 is a block diagram showing the processing involved in the fetal heartbeat monitoring system of the present invention.

FIG. 2 shows one embodiment of the sensor array in the system of the present invention.

FIG. 3 shows another embodiment of the sensor array of the present invention.

DETAILED DESCRIPTION OF THE INVENTION

Figure 4:
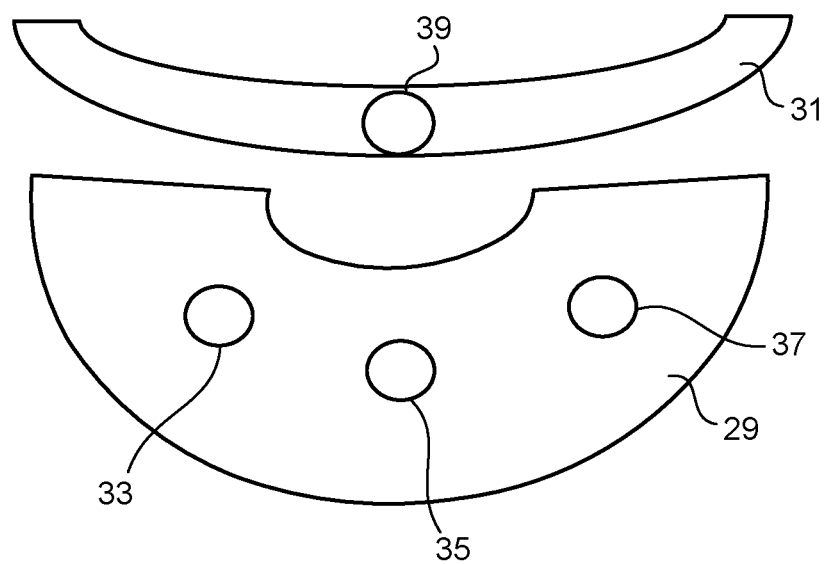
FIG. 4 shows a configuration of the sensor array as applied to separate wearable articles.

FIG. 1 shows the system 10 for the monitoring and recording of fetal heartbeat sounds in accordance with the system of the present invention. In particular, there is a sensor matrix 12 adapted to be positioned at, on, or adjacent to the mother's body. A signal conditioner 14 is connected to the sensor matrix 12 so as to condition the signal from the sensors, such as by filtering, by amplifying, and by other conditioning techniques. A sound dampening isolation layer 16 will be positioned on the back side of the sensor matrix 12 and the signal conditioner 14 so as to isolate sounds from the external environment relative from the sensor matrix 12. In particular, the sound dampening/isolation layer can be placed against the inside of the underwear or other wearable article worn by the mother. A multiplexer 18 is electrically connected to the signal conditioner 14 and the sensor matrix 12 so as to process the individual signals from each of the sensors of the sensor matrix 12. Twenty-four hour per day monitoring 20 can be connected to the multiplexer 18. Ultimately, the multiplexer 18 can be connected to a smartphone 22. The smartphone 22 can carry out the analog-to-digital conversion of the signal from the multiplexer 18. The smartphone 22 can also store information from the multiplexer 18. The smartphone 22 can include a processor, such as a central processing unit, a thermometer, data, time, GPS, and Bluetooth technology. An application 24 is cooperative at the smartphone 22. The application 24 can process information, can provide a graphical user interface, and can share data.

The system 10 of the present invention offers a great deal of convenience. For example, the system 10 can record on demand, provide twenty-four hour per day monitoring, and can record data on the smartphone 22. No additional battery is required. The system 10 can be multi-functional, such as identifying fetal position, fetal irritability, and other factors. Ultimately, the smartphone 22 will be interactive with the application 24.

The system 10 offers increased accuracy. Since the present invention is a passive system, and requires no doctor's intervention, it can record information very early, such as six weeks into the pregnancy term. The information relating to fetal heartbeat sound can be obtained regardless of the fetal positions. A full waveform is presented. Any background noise is effectively canceled so that an accurate fetal heartbeat sound can be determined.

The sensor matrix 12 can be arranged on the wearable article at any assigned position. The layout position of the sensor matrix 12 will be in accordance with the preferred design. FIGS. 2 and 3 illustrate two classical sensor array layout positions. The number of the sensor will be at least two. Each of the sensors in the sensor matrix 12 can be a piezoelectric button. This will function as a mini-sensor. As such, it can effectively function without much contact with the surface of the body of the mother.

FIGS. 2 and 3 show two preferred forms of the sensor matrix. FIG. 2 shows a cruciform array 26 of sensors 28, 30, 32, 34 and 36. In the preferred embodiment, the sensor 32 will be placed in correspondence with the location of the fetus. The sensors 28, 30, 34 and 36 that are placed in spaced relation to the sensor 32 so as to receive information from background noise and from the mother's heartbeat.

FIG. 3 shows a sensor array 38 having a rather trapezoidal form. As such, sensors 40 and 42 can be placed generally adjacent to the location of the fetus while the sensors 44 and 46 can be placed so as to obtain heartbeat information from the mother and sound information from the external environment.

FIG. 4 shows that there is a first wearable article 29 and a second wearable article 31 that are adapted to be placed upon the body of a mother in proximity to the fetus. The wearable article 29 can be in the nature of a belly band. Wearable article 29 can include sensors 33, 35 and 37 arranged in spaced relationship to each other. The wearable article 31 can include a sensor 39 thereon. Each of the wearable articles 29 and 31 can be wrapped around the stomach and/or chest of a mother so as to detect sound.

Figure 5:
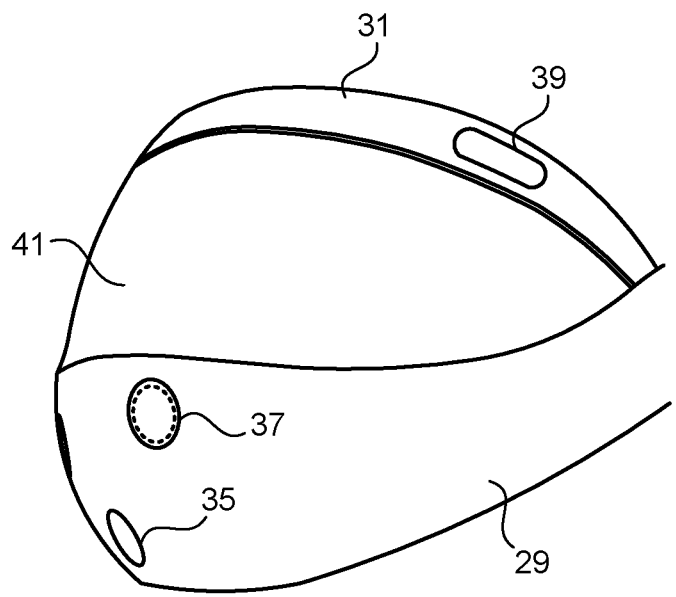
FIG. 5 is a perspective view showing the sensor array and wearable articles of the present invention is applied to the stomach of a mother.

FIG. 5 shows the wearable articles 29 and 31 as placed around the stomach 41 of a mother. The sensors 35 and 37 on the belly band of wearable article 29 are located in a lower part of the stomach of the mother so as to be in proximity to the fetus. Wearable article 31 will be placed above the stomach 41 in proximity to the heart of the mother. As such, sensor 39 will be directed so as to sense the heartbeat of the mother. Additional sensors can be provided so as to detect environmental sound.

Figure 6:
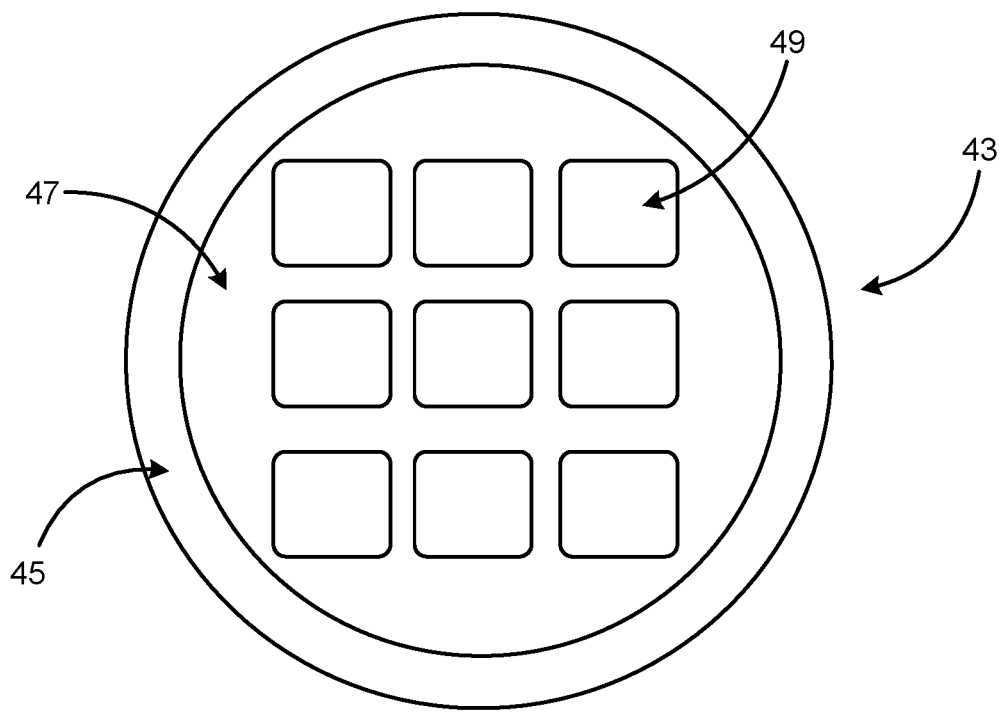
FIG. 6 is a plan view showing the sensor disk as used in the sensor array of the system of the present invention.

FIG. 6 shows the sensor disk 43 as used in the sensor array 12 of the present invention. The sensor disk 43 includes an annular metal disk 45 having an interior opening. A plurality of piezoelectric sensors 49 are positioned on the annular metal disk 45. A dampening material 47 is positioned on the annular metal disk 45 and between adjacent piezoelectric sensors 49. As such, the sound dampening material serves to isolate the piezoelectric sensors 49 from each other. As such, this configuration serves to isolate the piezoelectric sensor 49 from clothing or from contact with other surfaces.

Figure 7:
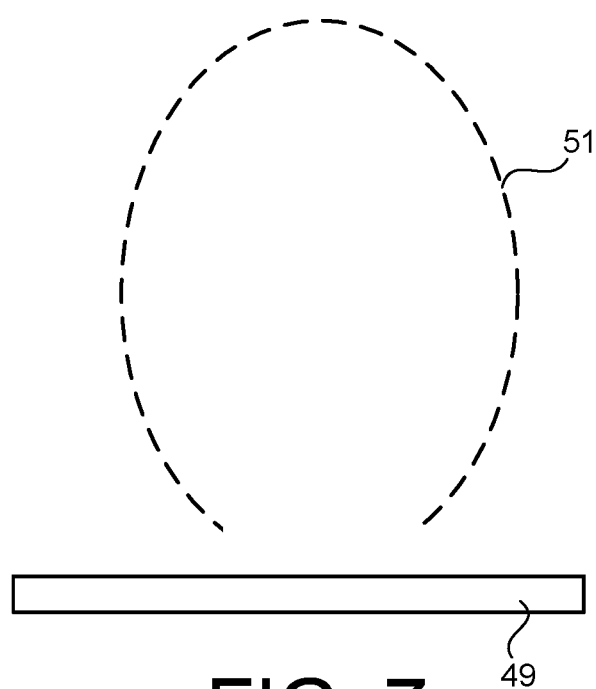
FIG. 7 is a diagram showing the sensor sensitivity polar pattern associated with the sensor of the present invention.

FIG. 7 shows the sensor sensitivity polar pattern 51 associated with the piezoelectric sensor 49. As can be seen, the sensor 49 will receive the sound as emitted in the area of the pattern 51. As such, this pattern 51 can be analyzed so as to determine the spatial relationships associated with the fetus and the fetal heartbeat.

Figure 8:
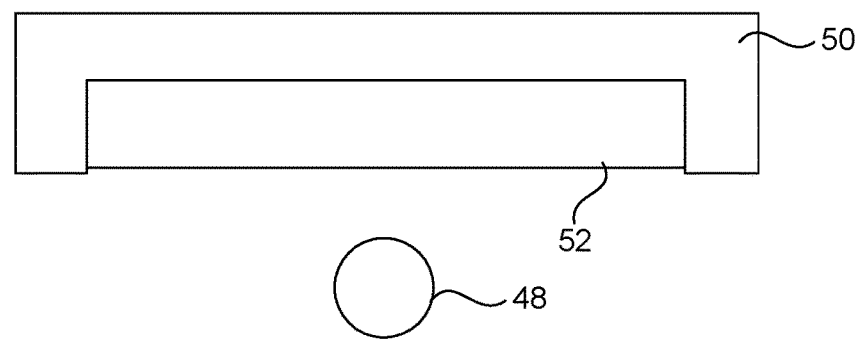
FIG. 8 shows the sound dampening/isolation layer as used in association with each sensor of the sensor array of the system of the present invention.

FIG. 8 shows the sound dampening/isolation layer 16 in relation to a sensor 48. The sound dampening/isolation layer can be used in association with each of the sensor. The sound dampening/isolation layer 16 will be provided for each sensor in the sensor matrix. The sound dampening/isolation layer 16 will be located between the sensor and the cloth/underwear of the mother. The layers of the sound dampening/isolation layer are a series of layers with different materials. The different materials can have different densities, thicknesses, and stiffnesses. The materials and thick, thickness and size can be a matter of design choice. FIG. 8 shows one realization of the sound dampening/isolation layer 16. In particular, in FIG. 8, there is a rubber layer 50 that can be placed adjacent to the underwear or other wearable article of the mother. A polymeric layer 52 can be placed interior of the rubber layer 50 and can be placed on the backside of the sensor 48. In particular, the polymer layer 52 can be made of a TEFLON™ material.

Figure 9:
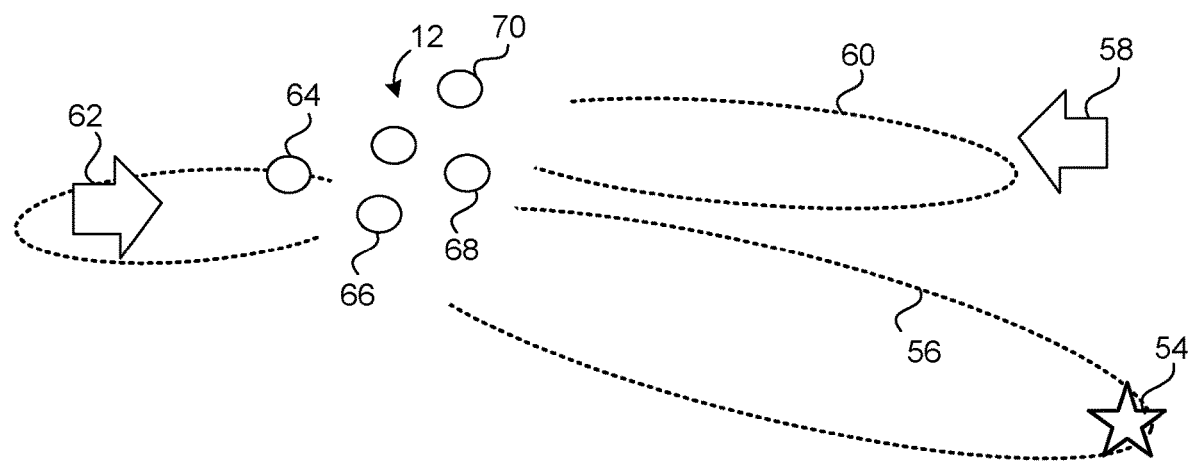
FIG. 9 is a diagrammatic illustration of the sensor array as used in receiving sound from various sources.

FIG. 9 shows how the system of the present invention passively detects fetal heartbeat sound. In particular, in FIG. 9, there is the sensor matrix 12 that has been placed on the body of the mother. These fetal heartbeat 54 transmits a sound wave 56 toward the sensor matrix 12. The mother's heartbeat 58 will transmit a sound signal 60 toward the sensor matrix 12. The environmental sounds and cloth-friction interference noise 62 is also transmitted to the sensor matrix 12. Because of the configuration of the array of the sensor matrix 12, certain sensors will predominantly receive sound from one of the sources. In particular, in FIG. 9, it can be seen that sensor 64 will receive more sound from the environmental or cloth-friction interference noise 62. Sensors 66 and 68 will receive more sound information from the soundwave 56 from the fetal heartbeat 54. This can provide a controllable monitoring beam for the different fetal positions. Sensor 70 can receive the soundwave 60 from the mother's heartbeat 58. By this array, comparisons can be made between the various signals received by the various sensor of the sensor matrix 12 so as to effectively process the various sound waves from the external interference noise 62, from the mother's heartbeat 58, and from the fetal heartbeat 54.

By the processing of signals in the manner shown in FIG. 9, information pertaining to the fetal heartbeat 54 can be obtained without the use of radiation. The system effectively isolates interference noise from the external environmental noise 62 and from the mother's heartbeat 58. The monitoring beam can be controlled for different fetal positions and complex situations. The fetal heartbeat tracking beam 56 is controllable so as to face the fetal heartbeat 54, to record the fetal heartbeat sound, or to face the interference sources to get background noise signals. These can be used to cancel the background noise during the processing. The target sound is recorded. The acoustic wave is process so as to obtain the target information. Hardware from the smartphone 22 for analog-to-digital conversion and memory storage can be used. All of the processing is carried out on the smartphone 22 and the application 24. The results can be shown in real-time and can also be reprocessed for other information. The system can be interactive in the application 24, for example, so as to determine the fetal position and a show sounds from different positions in the womb.

Figure 10:
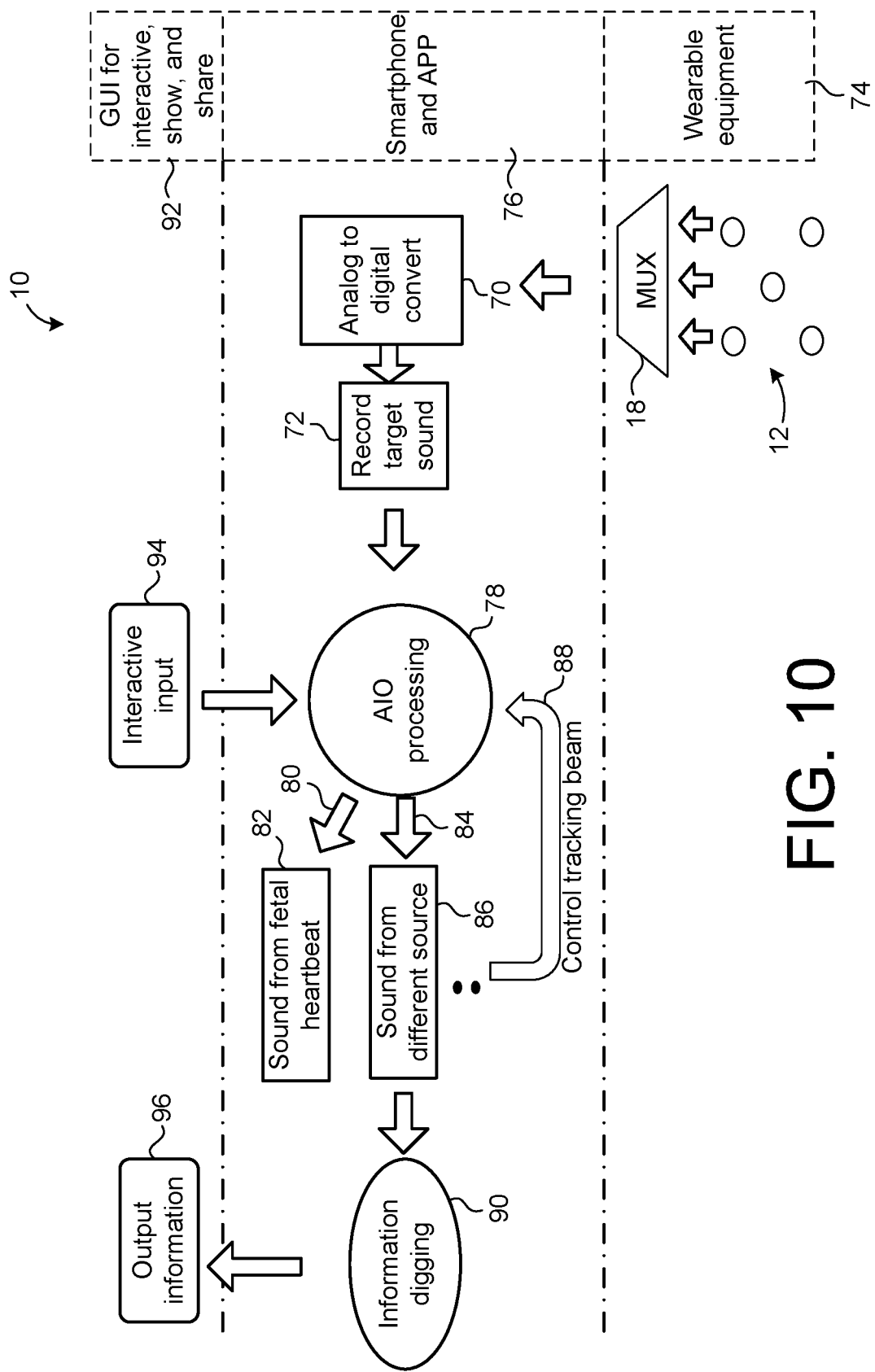
FIG. 10 is a block diagram showing the processing of sound as received by the sensor array in the system of the present invention.

FIG. 10 is a block diagram showing the system 10 of the present invention. Initially, it can be seen that the sensor matrix 12 transmits a signal to the audio-to-digital converter 70. The converted signal from the analog-to-digital converter 70 can be transmitted to a recorder 72 so as to record the target sound. The signal from the sensor matrix 12 can pass to the multiplexer 18. The multiplexer and the microphone matrix 12 are part of the "wearable" article 74. The smartphone 22 and application 24 are part of the processing system 76. As such, the smartphone 22 and the application 24 contain the analog-to-digital converter 70 and the recorder 72. The signal processor 78 receives the recorded target sound from recorder 72 and processes the sound. As such, the processor 78 can transmit a signal 80 so as to produce the sound from the fetal heartbeat 82. The processed signal can transmit a signal 84 which is the sound from different sources 86. A controlled tracking beam 88 can then return the sound from the different source 86 back to the processor 74. Ultimately, the sound from the different source 86 can be transmitted for information digging 90. A graphical user interface 92 can also be provided. The graphical user interface 92 can be interactive, can display, and can share the information. An interactive input 94 is cooperative with the processor 78 so as to control the information from the processor 78. The graphical user interface 92 can also display the output information 96.

Figure 11:
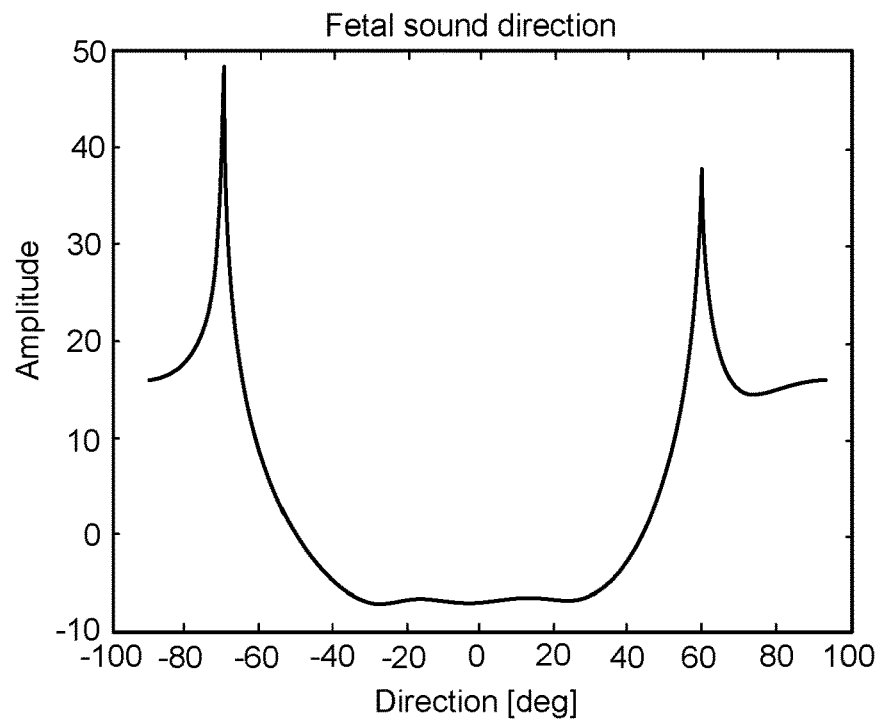
FIG. 11 is a graph showing the detection of fetal sound from other noise by the system of the present invention.

FIG. 11 is a graph illustrating how the fetal heartbeat can sound can be distinguished from other sound. It can be seen that the sensor matrix will receive an amplitude of sound and a direction of the sound. As can be seen, the fetal heartbeat can be the high-amplitude signal of the detected sound. This high-amplitude signal is located at approximately −70° from the sensor. Another high-amplitude signal can relate to the mother's's heartbeat. As such, the sensor array can determine that the mother's heartbeat is located at approximately +60° relative to the sensor array.

Figure 12:
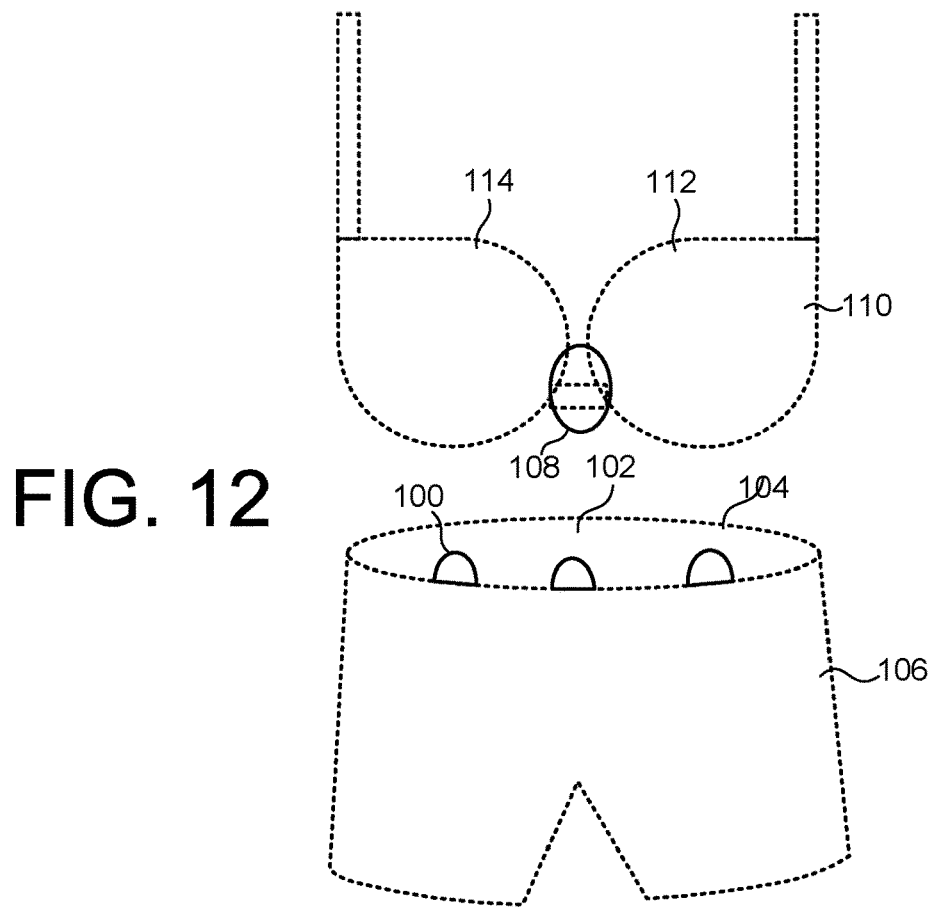
FIG. 12 is an illustration of an alternate manner of affixing the sensors to articles of clothing in the system of the poi.

FIG. 12 shows an alternative approach to the mounting of the sensor array relative to the body of the mother. It can be seen that there are a plurality of sensors 100, 102 and 104 that are secured at a top edge and inside of an upper edge of pants 106. Sensors 100, 102 and 104 are configured to face the fetus. Another sensor 108 is secured to bra 110 and between cups 112 and 114. Sensor 108 can face the heat of the mother.

Figure 13:
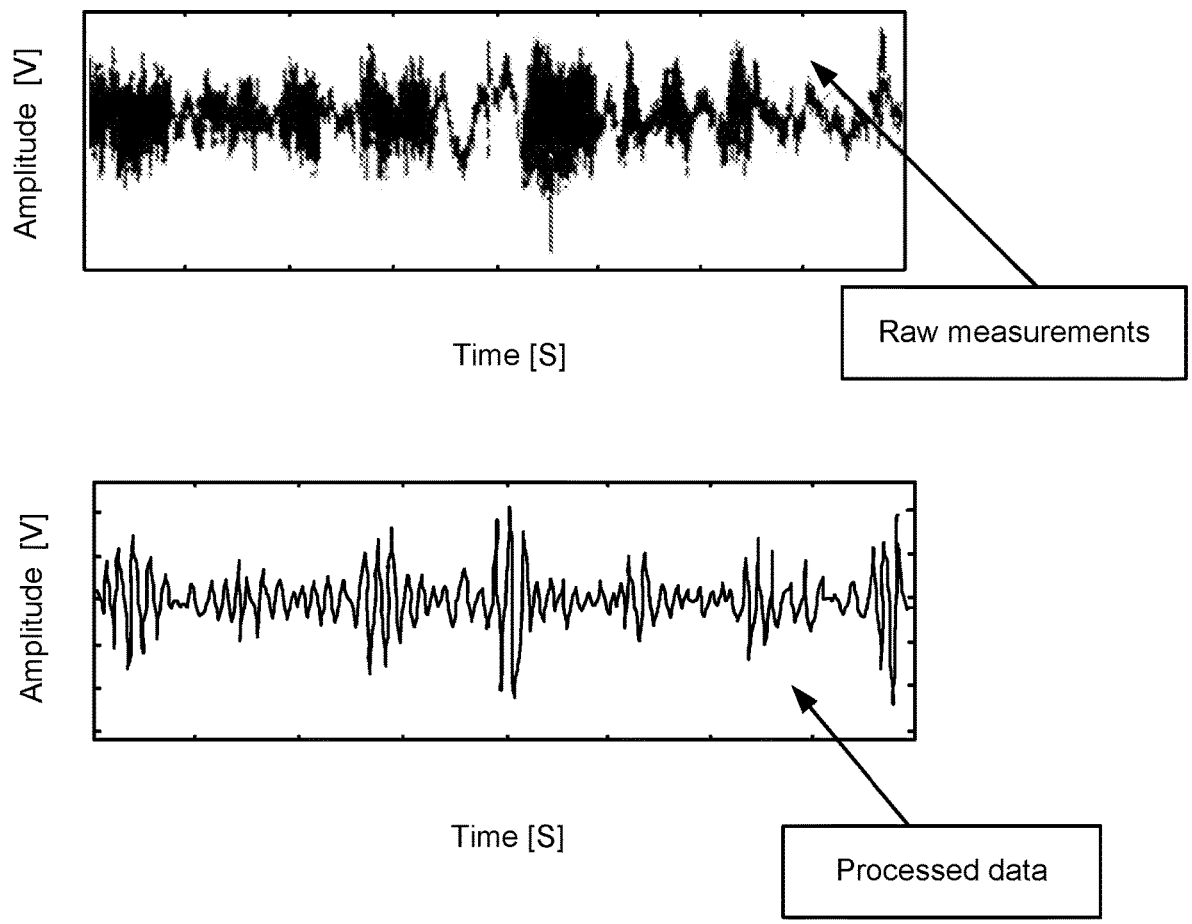
FIG. 13 shows graphs representing raw data and processed data as processed from the sensors.

FIG. 13 shows graphically the process of raw data so as to produce a waveform indication of the fetal heartbeat. As can be seen, the present invention is used for obtaining the fetal heart sound record and can also produce a full waveform. The system 10 of the present invention can provide the position of the fetal heartbeat along with personal health data, the fetal heart sound, the heart sound of the mother, information pertaining to the uterine contraction, fetal irritability and fetal position. Ultimately, the information digging can produce information pertaining to the sex of the child any potential health risk.

The foregoing disclosure and description of the invention is illustrative and explanatory thereof. Various changes in the details of the described structure and steps in the described method can be made within the scope of the appended claims without departing from the true spirit of the invention. The present invention should only be limited by the following claims and their legal equivalents.

We claim:

1. A system for monitoring a fetal heartbeat sound, the system comprising:
   a sensor matrix adapted to be placed adjacent to a fetus, said sensor matrix having a plurality of sensors of which at least one sensor is facing toward the fetus;
   a processor connected to said sensor matrix so as to receive signals transmitted by said sensor matrix, said processor adapted to identify the fetal heartbeat sound from among other sounds, said processor comparing the signals transmitted by the plurality of sensors against one another so as to assess an amplitude and direction of sounds sensed by said sensor matrix; and
   a display connected to said processor so as to provide a humanly perceivable indication of the fetal heartbeat sound.

2. The system of claim 1, said plurality of sensors arranged in spaced relation to each other.

3. The system of claim 1, further comprising:
   a wearable article adapted to be worn by a mother, said sensor matrix affixed to said wearable article.

4. The system of claim 3, said wearable article being a belly band adapted to be wrapped around a stomach of the mother.

5. The system of claim 4, further comprising:
   another wearable article positioned in adjustably spaced relation to said belly band, at least one of said plurality of sensors affixed to said another wearable article.

6. The system of claim 1, each of said plurality of sensors comprising:
   a metal disk; and
   a piezoelectric sensor positioned on said metal disk such that said piezoelectric sensor is acoustically isolated from said metal disk.

7. The system of claim 6, said piezoelectric sensor comprising a plurality of piezoelectric sensors positioned on said metal disk, the system further comprising:

a dampening material interposed between adjacent piezoelectric sensors of said plurality of piezoelectric sensors.

8. The system of claim 1, further comprising:
a signal conditioner connected to said sensor array so as to create a full waveform of sound.

9. The system of claim 1, each sensor of said plurality of sensors being a piezoelectric sensor.

10. The system of claim 1, said sensor array being in a trapezoidal pattern.

11. The system of claim 1, said sensor array being in a cruciform pattern.

12. The system of claim 1, said plurality of sensors of said sensor array having a controllable monitoring beam facing a heart of a mother so as to sense a heartbeat of the mother.

13. The system of claim 12, another sensor of said plurality of sensors facing an environment adjacent to the mother so as to sense background noise.

14. The system of claim 1, said processor comprising:
a multiplexer connected by wires or wirelessly to said sensor array.

15. The system of claim 14, said processor further comprising:
a smartphone or a personal digital assistant connected to said multiplexer so as to process signals from said multiplexer so as to isolate the fetal heartbeat sound from a heartbeat of a mother.

16. A method of monitoring a fetal heartbeat sound, the method comprising:
positioning a sensor array onto a body of a mother in proximity to a fetus;
detecting the fetal heartbeat sound and a heartbeat sound of the mother and environmental sound by said sensor array;
transmitting a plurality of signals from said sensor array to a processor;
processing the plurality of signals so as to isolate the fetal heartbeat sound from mother and the environmental sound, the step of processing comprising:
comparing the signals transmitted by the sensor array against one another so as to assess an amplitude and direction of sound sensed by the sensor array; and
displaying an indication of the fetal heartbeat sound from the processed plurality of signals.

17. The method of claim 16, further comprising:
affixing said sensor array onto a wearable article such that the sensor array is interposed between the wearable article and the body of the mother.

* * * * *